United States Patent [19]
Dossett

[11] Patent Number: 6,140,460
[45] Date of Patent: Oct. 31, 2000

[54] CATALYST COMPOSITION

[75] Inventor: Stephen John Dossett, Aldershot, United Kingdom

[73] Assignee: BP Chemicals Limited, London, United Kingdom

[21] Appl. No.: 09/413,261

[22] Filed: Oct. 6, 1999

Related U.S. Application Data

[62] Division of application No. 08/999,552, Dec. 3, 1997, Pat. No. 6,018,016, which is a continuation of application No. PCT/GB97/00963, Apr. 4, 1997.

[30] Foreign Application Priority Data

Apr. 4, 1996 [GB] United Kingdom .................. 9607246
Mar. 11, 1997 [GB] United Kingdom .................. 9704994

[51] Int. Cl.$^7$ .................................................. C08G 67/02
[52] U.S. Cl. ...................... 528/392; 528/397; 528/399; 556/7; 556/13; 556/136; 502/155; 502/162; 502/167
[58] Field of Search .................................. 528/392, 397, 528/399; 556/7, 13, 136; 502/155, 162, 167

[56] References Cited

PUBLICATIONS

Chen Abstract: 120:77437 "Preparation of New Monoflurophsphines and Some of Their Transitors Metal Complexes." "Meyer et al."

110:154524 "A New Approach to the Synthesis of Areyldifluorophshines." "Heuer et al."

127:319887 Group VIII Metal Catalyst Composition of the Syketone Manufacture "Dossett".

*Primary Examiner*—Duc Truong
*Attorney, Agent, or Firm*—Fay, Sharpe, Fagan, Minnich & McKee, LLP

[57] ABSTRACT

A catalyst composition prepared by reacting together
(a) a source of a Group VIII metal
(b) a bidentate phosphine ligand having at least two phosphorus atoms joined by a bridging group of the formula

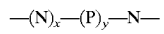

$$-(N)_x-(P)_y-N-$$

where x is 0 or 1 and y is 0 or 1, and
(c) a promoter is disclosed. The Group VIII metal is preferably palladium. The promoter can be a weakly or non-coordinating anion. Alternatively it can be a boron hydrocarbyl compound or an aluminoxane.

Also disclosed are novel bidentate phosphine ligands and intermediates therefor as well as novel palladium complexes. The catalysts are used in the preparation of polyketones.

8 Claims, No Drawings

CATALYST COMPOSITION

This application is a divisional of U.S. application Ser. No. 08/999,552 filed on Dec. 3, 1997 now U.S. Pat. No. 6,018,016, which is a continuation of International Application No. PCT/GB97/00963 filed on Apr. 4, 1997.

The present invention relates to a novel catalyst composition and to a process for the preparation of interpolymers of olefins and carbon monoxide by polymerising a mixture of one or more olefins and carbon monoxide in the presence of such catalyst compositions.

The preparation of linear alternating interpolymers of olefins and carbon monoxide having the formula:

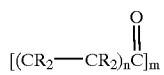

where the R groups are independently hydrogen or hydrocarbyl groups, n is at least 1 and m is a large integer, is known from U.S. Pat. No. 3,694,412. Such linear alternating interpolymers, which hereinafter will be referred to as polyketones, are prepared according to U.S. Pat. No. 3,694,412 by polymerising a mixture of one or more olefins and carbon monoxide in the presence of palladium halide and an inert solvent. However, the process described in U.S. Pat. No. 3,694,412 is slow even at elevated temperature and pressure.

An improved version of the process described in U.S. Pat. No. 3,694,412 is described in European patent applications 181014 and 121965.

It was subsequently found that the rate of the polymerisation process could be increased considerably by using a palladium catalyst with inter alia a bidentate phosphine and the anion of a carboxylic acid having a pKa of less than 2 (as measured in aqueous solution). Examples of anions which can be used include trichloroacetate, dichloroacetate, tetrafluoro-borate, hexafluorophosphate p-toluene sulphonate, and borosalicylate such anions being respectively the conjugate anions of trichloroacetic acid, dichloroacetic acid, tetrafluoroboric acid, hexafluorophosphoric acid, p-toluenesulphonic acid and borosalicyclic acid.

More recently the use of hydrocarbyl boranes as effective promoters in palladium catalysed polyketone synthesis has been disclosed in EP 619335.

It has now been found that instead of using a bidentate phosphine as described in EP 121965, catalyst systems, in particular palladium catalyst systems, based upon novel phosphine ligands can be employed.

According to the present invention, there is provided a catalyst composition prepared by reacting together:

(a) a source of a Group VIII metal,
(b) a bidentate phosphine ligand having at least two phosphorus atoms joined by a bridging group of the formula:

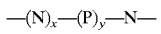

where x is 0 or 1 and y is 0 or 1, and
(c) a promoter.

The present invention further provides a process for preparing polyketones by polymerising a mixture of carbon monoxide and one or more olefins in the presence of a catalyst composition as defined hereinabove.

The term polyketone is used herein to mean an interpolymer of one or more olefins with carbon monoxide. The idealised structure of such a material would comprise a one, two or three dimensional network of strictly alternating olefin and carbon monoxide units. Although polyketones prepared according to the present invention correspond to this idealised structure, it is envisaged that materials corresponding to this structure in the main but containing small regimes (ie up to 10 wt %) of the corresponding polyolefin also fall within the definition.

The catalyst composition described above is itself prepared by reacting together (a) a source of Group VIII metal, (b) a bidentate phosphine ligand having the formula as shown above, and (c) a promoter.

As regards component (a), this is a Group VIII metal; the Group VIII metals are iron, cobalt, nickel, ruthenium, rhodium, palladium, osmium, iridium and platinum. The second row Group VIII metals (ie ruthenium, rhodium and palladium) are preferred; particularly preferred is palladium.

As regards component (b), this is a bidentate phosphine ligand having at least two phosphorus atoms joined by a bridging group of the formula

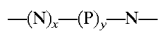

where each of the N atoms which may constitute part or all of the bridge between the said two phosphorus atoms are trivalent and the P atom that may constitute part of the bridge between the said two phosphorus atoms (i.e. y=1) is trivalent or pentavalent. Where all the atoms in the bridge whether N or P are trivalent, two of the three bond of each of the atoms that constitute the bridge are directed to adjacent atoms. The third bond can be directed to an adjacent atom in the bridge (to give a double bond in the bridge), but is more likely to be directed to a monovalent, preferably organic, group which is directly bonded to the respective bridge atom but which does not form part of the bridge itself.

Where y=1, the phosphorus atom forming part of the bridge may alternatively be pentavalent in which case two of the bonds are directed to the adjacent atoms to form part of the bridge. The other three bonds can for example be directed to three monovalent groups or preferably to one monovalent group and a double bond for example to oxygen or sulphur.

The bridging group is likely to be of the formula —(NR$^2$)$_x$—(PR$^3$)$_y$—NR$^2$— where each R$^2$ is the same or different and R$^2$ and R$^3$ represent a monovalent, preferably organic, group and x and y are independently 0 or 1. In particular component (b) can be a compound of formula I:

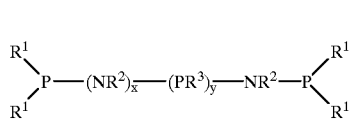

(I)

where R$^1$ may be the same or different and is an organic group, R$^2$, R$^3$, x and y are defined above.

R$^1$ is an organic group and may be hydrocarbyl (for example aryl, alkyl), alkoxy, amido and substituted derivatives thereof. Where R$^1$ is alkyl, it is preferably a C$_1$ to C$_6$ alkyl group, especially ethyl. Where R$^1$ is aryl, it is for example phenyl or an aromatic group substituted at one or both ortho positions with respect to the phosphorus atoms with a polar substituent for example an alkoxy or an amido group for example a methoxy group for example o-anisyl preferably o-anisyl. Where R$^1$ is alkoxy, R$^1$ may suitably be OC$_6$H$_5$. Where R$^1$ is NR$^4{}_2$, R$^4$ may suitably be alkyl.

Alternatively more than one of the R$^1$ groups may be linked to form a cyclic structure in which case the two phosphorus atoms and the —(N)$_x$—(P)$_y$—N— bridge would form part of such a cyclic structure. A particular example of this type of ligand would be cyclotetraphosphazenes of the formula $[NR^2PR^3]_4$ or compounds of the formula $[NR^2PR^3NR^2PR^3NR^2PR^3]$ where $R^2$ and $R^3$ have the meanings given herein.

$R^2$ and $R^3$ are monovalent groups, preferably monovalent organic groups. For example $R^2$ can be hydrogen or a hydrocarbyl group, preferably a $C_1$ to $C_6$ alkyl group, for example methyl or ethyl or an aryl group preferably phenyl.

$R^3$ can be a hydrocarbyl group or substituted hydrocarbyl, preferably a $C_1$ to $C_6$ alkyl group. Alternatively, $R^3$ is an aryl group for example phenyl or substituted phenyl.

Alternatively $R^2$ and/or $R^3$ can be a hetero group e.g. $OR^5$, $SR^5$ or $NR^6_2$ where $R^5$ and $R^6$ are independently a hydrocarbyl group e.g. OMe, OEt, OPh, $NMe_2$, $NEt_2$ etc. It is a feature of the hetero group that the group is bonded to the bridge atoms directly through a hetero atom.

As regards x and y, these are independently 0 or 1. Preferably x and y are both 0 in which case component (b) comprises a PNP unit. (Two phosphorus atoms with a single N atom as a bridge).

The ligands can be prepared using procedures known to the man skilled in the art and disclosed in published literature.

Ligands of the formula $(R^1)_2PNR^2P(R^1)_2$ (i.e. x=y=0) can be prepared by reacting 2 moles of $R^1_2P$ (halide) with $NH_2R^2$ in the presence of a base (for example $NR_3$), $R^1_2P$ (halide) is preferably $R^1_2PCl$. A range of $R^1_2PCl$ are available commercially but can also be made by reacting $R_2NPCl_2$ where R is a hydrocarbyl group for example Me or Et with $LiR^1$ or the corresponding Grignard reagent. $R_2NPCl_2$ can be obtained commercially or obtained by reacting $NHR_2$ and $PCl_3$. In the case of $R^1_2PCl$ where $R^1$ is o-anisyl, $R^1_2PCl$ can be prepared by reacting a solution of o-anisyl lithium in THF/hexane with $R_2NPCl_2$ where R is a hydrocarbyl group for example, Me, Et or isopropyl and treating the subsequent (o-anisyl)$_2$ $PNR_2$ with a Bronsted acid, preferably anhydrous HCl. The advantage of using o-anisyl lithium (as opposed to the corresponding Grignard reagent) is that the final $R^1_2PCl$ product is easier to purify and extract. Where $R^1$ is o-anisyl the reaction of $R^1_2P$ (halide) with $NH_2R^2$ in the presence of a base to give $(R^1)_2PNR^2P(R^1)_2$ is preferably effected using methylamine i.e. $R^2$=Me and preferably in dichloromethane.

It is also possible to react $NH_2R^2$ with 1 mole of $R^1_2P$ (halide) in the presence of base to generate $R^1_2PNHR^2$ which can then be further reacted in the presence of base with one mole of $R^1_2'P$(halide) where $R^1 \neq R^1{}'$ to give an unsymmetrical bisphosphine of the formula $R^1_2PNR^2PR^1{}'_2$, for example where $R^1$=phenyl, and $R^1{}'$=o-anisyl and $R^2$=n-butyl.

The compounds (o-anisyl)$_2$P(halide), its preparation and ligands of the formula $(R^1)_2P—(N)_x—(P)_y—N—P(R^1)_2$ in particular $(R^1)_2PN(R) P(R^1)_2$ where at least one of groups $R^1$ is an o-anisyl group and R is a hydrocarbyl group are novel and consequently form part of the present invention.

Ligands where x=1 y=0 i.e. having a bridging group of —N—N— can be prepared as described in Inorganic Chemistry 1995 (34) 5483–5488.

Ligands where x=1 y=1 i.e. having a bridging group of —N—P—N can be prepared as described in J. Chem Soc. (A) 1967 1492–1498 and J. Chem Soc (A) 1970, 2715–2719.

An alternative method of preparing $R^1_2$ PCl is to react $PCl_3$ with the corresponding $R^1$ Grignard reagent in THF followed by precipitation of magnesium halide by-product by adding dioxan. The corresponding $R^1_2PNRPR^1_2$ can be made by further reacting the product of the first step with $H_2NR$ in the presence of a base (e.g. $NR_3$) in THF.

As regard component (c) which is a promoter, this can be a source of an anion which is either non-coordinating or weakly coordinating. Such anions are suitably the conjugate bases of strong acids having eg a pKa of less than 6, preferably less than 2 (eg. $HBF_4$, $HPF_6$, $HSbF_6$, paratoluene sulphonic acid). Alternatively, the promoter can be a boron hydrocarbyl compound for example a boron alkyl, or boron aryl compound. In particular the Boron hydrocarbyl compound can be a Lewis acid of the formula BXYZ where at least one of X, Y and Z is a monovalent hydrocarbyl group. Where any one of X, Y or Z is a monovalent hydrocarbyl group, it is suitably an alkyl, for example a $C_1$ to $C_6$ alkyl group, or an aryl group for example a substituted or unsubstituted phenyl group for example $C_6H_5$ or $C_6F_5$. Other suitable monovalent hydrocarbyl groups are p-Hal $C_6H_4$ (where Hal=F, Cl, Br), m, m—$C_6H_3(CF_3)_2$, $CF_3$ and $C_2F_5$. It is to be understood that two or three of the groups X, Y and Z can together form bi or trivalent groups respectively. At least one of X, Y and Z is a monovalent hydrocarbyl group, however it is preferred that at least two, preferably three of X, Y and Z are each monovalent hydrocarbyl groups. Suitable examples of such Lewis acids are $BMe_3$, $BEt_3$, $B(C_6H_5)_3$, $B[m,m—(CF_3)_2 C_6H_3]_3$, $B(mesityl)_3$, $B(p-Hal C_6H_4)_3$ (where Hal=F, Cl, Br), $B(m-CF_3C_6H_4)_3$ and $B(C_6F_5)_3$, preferably $B(p-HalC_6H_4)_3$, $B(C_6H_5)_3$ and $B(C_6F_5)_3$. Where one or more of X, Y and Z is not a hydrocarbyl group, it is suitably a OH, OR or halide group, preferably a halide group, for example fluoride, chloride and bromide, especially fluoride. Examples of compounds where one of X, Y, Z is a group other than a hydrocarbyl group are boronic acids of the formula $RB(OH)_2$ where R is a hydrocarbyl group eg PhB $(OH)_2$ and hydrocarbyl 1,3,2-benzodioxaboroles.

Other suitable boron hydrocarbyl compounds for use in this invention are borate salts of the formula $MBR_4$ where M is an alkali metal eg Li, Na and at least one of the groups R is a hydrocarbyl group (eg $C_6H_5$, $C_6F_5$ and substituted analogues). For example, a suitable compound could be $LiB(C_6F_5)_4$ or $NaB(C_6H_5)_4$. Where one or more of the R groups is not a hydrocarbyl group it is suitably an OH, OR or halide group for example OH. A typical example of such a compound is $NaBPh_3(OH)$.

When a boron hydrocarbyl compound is used, for example a Lewis Acid BXYZ, it is added to the reaction medium in an amount such that the Group VIII metal:boron ratio is in the range 10:1 to 1:200, preferably 1:1 to 1:100, most preferably 1:5 to 1:70 eg 1:50.

The boron hydrocarbyl compound can be added in a single addition, preferably at the beginning of the polymerisation reaction, in several discrete additions throughout the reaction or continuously.

Alternatively the promoter could be anion containing a plurality of boron atoms such as those disclosed in EP 702045.A2 or an aluminoxane.

Where the Group VIII metal is palladium, the source of palladium can include simple inorganic and organic salts, eg halides, nitrates, carboxylates and the like as well as organometallic and coordination complexes. In some cases, by suitable choice of coordination complex, it may be possible to add the palladium and the compound of formula I as a single entity.

In addition to the bidentate phosphine ligand, the Group VIII metal compound may preferably comprise other groups or ligands bonded to the Group VIII metal; these groups or ligands may or may not derive from any Group VIII metal precursors that have been used in generating the Group VIII metal compound. Such groups or ligands are suitably halides, especially chloride; acetate, trifluoroacetate, tosylate, nitrate, sulphate, acetyl acetonate, cyanide, preferably acetate or labile ligands e.g. trifluoroacetate, tosylate, nitriles, solvent molecules e.g. water, acetone.

The Group VIII metal compound can suitably be a neutral or cationic compound

  (II)

or

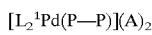  (III)

where each L is independently a monodentate ligand or $L_2$ taken together is a bidentate ligand and P—P is a bidentate phosphine ligand having at least two phosphorus atoms joined by a bridging group of the formula —$(N)_x(P)_y$—N— as defined above for example —$(NR^2)_x$—$(PR^3)_y$—$NR^2$— where each $R^2$ is the same or different and is a hydrogen or hydrocarbyl group, $R^3$ is a hydrocarbyl group and x and y are independently 0 or 1. Alternatively $R^2$ and $R^3$ can independently be hetero groups. In particular a compound of the formula I where $R^1$, $R^2$ and $R^3$ have the meanings assigned to them as hereinabove, can be used as P—P. L is typically a halide or carboxylate, for example $CH_3COO$ or $CF_3COO$. With regard to compounds of Formula III, $L^1$ is typically a neutral ligand such as, benzonitrile, acetonitrile, diethyl ether, or water. A is a weakly coordinating or non-coordinating anion as defined under component (c) above or $(A)_2$ together can be a weakly or non-coordinating dianion. In a further aspect of the present invention there are provided compounds of formulae II or III as defined above provided that in the case of compounds of formula II when P—P is a bidentate ligand having at least two phosphorus atoms joined by a bridging group of the formula —$(N)_x$—$(P)_y$—N where x=0, y=0 (i.e. single nitrogen atom in the bridge), L is not Cl and when L is Cl, and PP is $(R^7)_2PN(Me)N(Me)P(R^7)_2$, $R^7$ is not alkoxy. Particular examples of compounds of formulae II and III are $[Pd\{Ph_2PN(Me)N(Me)PPh_2\}Cl_2]$ and $[Pd\{Ph_2PN(Me)N(Me)PPh_2\}(PhCN)_2][BF_1]_2$.

Where the promoter is a non-coordinating or weakly coordinating anion, this can also be incorporated into a discrete compound as a counter anion as in compounds of Formula III. Alternatively, the anion can be used in the form of a salt or its conjugate acid together with the Group VIII metal and the compound of formula I whether the latter two are added as a single discrete compound or are added as two compounds.

Although any source of the Group VIII metal can be used, it may be necessary when a metal complex having strongly coordinating ligands is employed, to ensure that such ligands are removed. An example of such a complex is palladium acetate where the acetate anions bind to the palladium. In such cases the acetate anions can be removed by adding component (c) above as the conjugate acid of a non-coordinating or weakly coordinating anion since such a conjugate acid will protonate the acetate anions and cause their removal.

Alternatively, when metal halides eg palladium halides are used it is preferred to use a thallium or silver salt of a non-coordinating or weakly coordinating anion. In such cases a metathesis reaction occurs and the insoluble silver or thallium halide precipitates and can be removed by filtration.

It is possible to use these techniques to transform compounds of Formula II into compounds of Formula III. The removal of the coordinating ligands such as chloride or acetate is effected as described above in the presence of a neutral ligand $L^1$ e.g. benzonitrile. Removal of the coordinating ligand and addition of the neutral ligand is concomitant with addition of weakly or non-coordinating anions to give the compounds of Formula III.

With regard to the polymerisation reaction using the catalyst composition herein described, a feedstock comprising an source of carbon monoxide may be used. Thus, the carbon monoxide may contain nitrogen, inert gases and up to 10% hydrogen. Any olefin, can in theory, be used although the best reaction rates are obtained when either ethene or a mixture of olefins, for example ethene propene and the like is used. The lower rates obtained in the absence of ethene should not be construed as indicating that the process can only be used with an ethene feedstock since other olefins such as propene, 4,methylpentene-1, styrene, acrylates, vinyl acetates and the like all undergo reaction to some extent. A preferred polyketone is a terpolymer of ethene, propene and carbon monoxide; under these circumstances the olefin will be a mixture of ethene and propene.

It is a feature of the present invention that where carbon monoxide is polymerised with a mixture of more than one olefin in particular ethylene and a second α-olefin for a given ethylene/α-olefin ratio in the feedstock polyketones prepared using the catalyst composition of the present invention have higher α-olefin contents than polyketones prepared using prior art catalyst compositions. This allows the α-olefin charge to be reduced for a given α-olefin content in the final polymer.

The catalyst composition can be used in either the gas phase or the liquid phase. It is to be understood that the term liquid phase also includes slurry phase where the polyketone product is insoluble in the reaction solvent.

Where the polymerisation is carried out in the gas phase, it is preferred to support the catalyst on a carrier which can be for example polyketone polymer or an inorganic carrier for example alumina or silica. Where the polymerisation process is carried out in the liquid phase, it is suitably carried out in a solvent which is chemically inert under the conditions employed and one in which the catalyst is soluble. Moreover, the solvent like the anion should preferably be either weakly coordinating or non-coordinating. Examples of such solvents include alcohols eg methanol, ethanol, propanol, ethers, glycol ethers and chlorinated solvents eg chloroform and dichloromethane. Preferred solvents are methanol, ethoxyethanol, chloroform or dichloromethane, especially dichloromethane. Alternatively, an aliphatic tertiary alcohol can be used, preferably tertiary butanol. This can be used as a solvent on its own or in combination with an aprotic solvent eg ketones. A preferred solvent system is tertiary butanol/acetone mixture. It is also possible to use hydrocarbon solvents e.g. alkane (pentane, hexane, cyclohexane) or olefins especially where the olefin is a coreactant. The solvent may contain small quantities of water for example up to about 5% wt/wt.

The polymerisation process is suitably carried out at temperature in the range of from 20 to 150° C., preferably 50 to 120° C. and at elevated pressure, eg 1 to 100 bar. The overpressure of gas is suitably carbon monoxide or carbon monoxide and olefin, if the olefin is gaseous under the reaction conditions. The process may be operated batchwise continuously or in cascade.

The invention will be illustrated with reference to the following examples.

EXAMPLE 1

$Et_2PN(^nBu)PEt_2$ was prepared as follows:

$PEt_2Cl$ (0.589 g, 4.7 mmol) was added dropwise to a $Et_2O$ solution (20 cm$^3$) of $NH_2{}^nBu$ (0.173 g, 2.4 mmol) containing $NEt_3$ (1.4 g) and stirred for one hour. During this time a white precipitate was formed. The supernatant containing the product was filtered and the solvent removed in vacuo yielding $Et_2PN(^nBu)PEt_2$ as a clear liquid (0.499 g, 2.0 mmol). $^{31}P[^1H]$ NMR $(CD_2Cl_2)$=58.0 ppm.

EXAMPLE 2

$Ph_2PN(^nBu)PPh_2$ was prepared as detailed in Example 1 with the following changes. $Ph_2PCl$ (1.0 g, 4.5 mmol) was added dropwise to a $Et_2O$ solution (20 cm$^3$) of $NH_2{}^nBu$ (0.173 g, 2.4 mmol) containing $NEt_3$ (1.4 g) and stirred for 1 hour, yielding $Ph_2PN(^nBu)PPh_2$ (0.848 g, 1.92 mmol) of product. $^{31}P[H]$ NMR $(CD_2Cl_2)$=63.0 ppm.

EXAMPLE 3

$(PhO)_2PN(Me)N(Me)P(OPh)_2$ was prepared following the general procedure as detailed in Chem. Ber. 1994, 127, 1355. A mixture of corresponding alcohol (82.0 mmol) and $Et_3N$ (84.0 mmol) in n-hexane (50 ml) was added dropwise to $(Cl_2PN(Me)N(Me)PCl_2)$ (20.5 mmol) also in n-hexane (200 ml) at 25° C. The reaction mixture was stirred for 2 hours and the $Et_3NHCl$ was filtered off. Removal of the solvent in vacuo gave the analytically pure compound in 75–90% yield as a viscous liquid.

EXAMPLE 4

$[Pd\{Ph_2PN(Me)N(Me)PPh_2\}(PhCN)_2][BF_4]_2$ was prepared as follows:

Phenylmagnesium bromide (3 m in $Et_2O$)(9.563 gms, 30.6 mmol) was added dropwise to a solution of $Cl_2PN(Me)N(Me)PCl_2$(2.0 gms 7.6 mmol) in $Et_2O$ (50 cm$^3$) over a period of 30 mins. Stirring was continued for a further 30 mins, after which time the solids were allowed to settle. The supernatant was transferred to a second vessel containing $[PdCODCl_2]$(1 gm, 3.5 mmol) in $CH_2Cl_2$ (50 cm$^3$) via filter cannula and the reaction monitored by $^{31}P$ nmr. When the addition was complete the solution was filtered through celite and the solvent removed in vacuo, affording $[Pd\{Ph_2PN(Me)N(Me)PPh_2\}Cl_2]$ as a yellow powder (1.9 gms 3.1 mmol).

A solution of $[Pd\{Ph_2PN(Me)N(Me)PPh_2\}Cl_2]$ (0.393 gms, 0.6 mmol) in $CH_2Cl_2$ (20 cm$^3$) was added dropwise to a suspension of $AgBF_4$ (0.379 gms, 1.9 mmol) in $CH_2Cl_2$ (20 cm$^3$) containing PhCN (0.6 mls). A precipitate was immediately formed and stirring maintained for 30 mins. After this time the solids were allowed to settle and the supernatant filtered through celite. Removal of the solvent in vacuo yielded $[Ph\{Ph_2PN(Me)N(Me)PPh_2\}(PhCN)_2][BF_4]_2$ (0.411 g, 0.4 mmol) as a yellow powder.

$^{31}P\{^1H\}$ NMR $(CD_2Cl_2)$=137.5 ppm.

EXAMPLE 5

$Ph_2PN(Et)P(Ph)N(Et)PPh_2$ was prepared as follows.

A solution of $NH_2Et$ (2 m in THF) (50 cm$^3$, 0.1 mol) was added dropwise to a solution of $PhPCl_2$ (3.0 g, 16.7 mmol) in $Et_2O$ (50 cm$^3$ at 0° C. Immediately a precipitate as formed and the mixture was stirred overnight. The suspension was then filtered through celite, the supernatant collected and the solvent removed in vacuo. The resultant yellow oily residue was transferred to a vacuum distillation apparatus and distilled. A fraction, collected at ca 50° C. 10$^{-2}$ mmHg was characterised as being the desired product, namely PPh (NHEt)$_2$ (0.64 g, 3.3 mmol).

A solution of PPh (NHEt)$_2$ (0.301 g, 1.5 mmol) in $CH_2CH_2$ (20 cm$^3$) was added to $PPh_2Cl$ (0.677 g, 3.0 mmol) dissolved in $CH_2Cl_2$ (5 cm$^3$) containing $NEt_3$ (0.466 g, 4.6 mmol) and stirred for two hours. The solvent was removed in vacuo affording an off white solid. The solid was washed with 3×20 cm$^3$ aliquots of diethylether, the washings combined and the solvent then removed in vacuo yielding a white solid characterised as $Ph_2 PN(Et)P(Ph)N(Et)PPh_2$ (0.540 g, 1.3 mmol) $^{31}P[H]$ NMR $(CD_2Cl_2)$=53.5 [d, $PPh_2$, 2P, J (PP)25]. 105.1 [t, PPh, J(PP) 25 Hz] ppm.

EXAMPLE 6

A copolymer of carbon monoxide and ethene was prepared as follows.

$CH_2Cl_2$ (110 cm$^3$) was charged to a 300 cm$^3$ autoclave under nitrogen. The autoclave contents were pressurised to 30 bar G with a 1:1 mixture of carbon monoxide and ethene and heated to 70° C. A solution of $B(C_6F_5)_3$ (0.161 g, 0.310 mmol) in $CH_2Cl_2$ (10 cm$^3$) was introduced followed by a procatalyst solution comprising $Et_2 PN(^nBu) PEt_2$ (0.0039 g, 0.015 mmol) prepared as detailed in Example 1 and palladium acetate (0.0035 g, 0.015 mmol) in $CH_2Cl_2$ (10 cm$^3$). The pressure was adjusted to 50 bar G by the addition of a 1:1 carbon monoxide/ethene mixture and this pressure maintained by the addition of the aforementioned gas mixture on demand. After three hours, the pressure was released and the reaction was cooled to room temperature. The polymer was collected by filtration and dried under reduced pressure. 0.5 g of copolymer was obtained.

EXAMPLE 7

The procedure of Example 6 was repeated using $Ph_2PN(^nBu)PPh_2$ (0.0069 g, 0.016 mmol) prepared as detailed in Example 2 and palladium acetate (0.0035 g, 0.015 mmol). 6.823 of polymer was obtained.

EXAMPLE 8

The procedure of Example 6 was repeated using a procatalyst solution of $(PhO)_2PN(Me)N(Me)P(OPh)_2$ (0.010 g, 0.020 mmol) prepared as detailed in Example 3 and palladium acetate (0.0045 g, 0.020 mmol). A trace amount of polymer was obtained.

EXAMPLE 9

The procedure of Example 6 was repeated using a procatalyst solution of $Ph_2PN(Et)P(Ph)N(Et)PPh_2$ (0.0089 g, 0.016 mmol) prepared as detailed in Example 5 and palladium acetate (0.0035 g, 0.015 mmol). 4.070 g of polymer was obtained.

EXAMPLE 10

Carbon monoxide/ethene co-polymer was prepared by substantially the same procedure to that detailed in Example 6, with the following differences:

The procatalyst solution was comprised of $[Pd\{Ph_2PN(Me)N(Me)PPh_2\}(PhCN)_2][BF_4]_2$ (0.0143 g, 0.016 mmol), as prepared in Example 4. 1.340 g of polymer was obtained.

EXAMPLE 11

A carbon monoxide/ethene/propene ter-polymer was prepared by substantially the same procedure to that detailed in Example 6, with the following differences.

The autoclave was initially charged with $CH_2Cl_2$ (90 cm$^3$) and propene (24.58 g 0.58 mol). The procatalyst solution was comprised of $Ph_2PN(^nBu)PPh_2$ (0.0069 g, 0.015 mmol), prepared in Example 2, and palladium acetate (0.0035 g, 0.015 mmol). 1.01 gms of polymer was obtained, containing 10.5 mole % of propylene.

EXAMPLE 12
Preparation of $NMe\{P(C_6H_4OMe-2)_2\}_2$

Addition of a solution of diisopropylamine [25.30 g, 0.25 mol] in ether [40 ml] to a solution of phosphorus trichloride [10.90 ml, 125 mmol] in the same solvent [40 ml] at $-10°$ C. resulted in the rapid formation of a white precipitate. The mixture was stirred for two hours and then allowed to warm to room temperature. Stirring was continued for a further hour and the mixture then filtered through celite to give an etheral solution containing the product, $Cl_2PN^1Pr_2$ 1 Removal of the solvent in vacuo afforded the product [20,262 g 0.2 mol] as a pale yellow oil. $^{31}P\{^1H\}$ nmr $(CF_2Cl_2)\delta p=170$ ppm.

BuLi [1.81 ml of a 2.21M solution in hexanes, 4 mmol] was added to a solution of anisole [432 mg, 4 mmol] in THF [5 ml] and then stirred at room temperature for 2 hours. The resulting solution of o-anisyl lithium was then added to a solution of 1 [404 mg, 2 mmol] in ether, and stirred at room temperature overnight to give a mixture containing the product, $Ar_2PN^1Pr_2$ as the only phosphorus containing species. $^{31}P\{^1H\}$ nmr $(CD_2Cl_2)\delta p=21$ ppm.

Anhydrous HCl [4 ml of 1M solution in ether, 4 mmol] was then added to the mixture obtained above immediately forming a white precipitate. The resultant slurry was stirred at room temperature for 2 hours after which time the solvent was removed in vacuo. The residue was extracted with toluene and the slurry filtered through celite to yield a pale yellow solution containing the desired compound, $Ar_2PCl$ 2. Removal of the solvent in vacuo afforded 2 as a pale yellow solid. (505 mgs, 1.8 mmol) $^{31}P\{^1H\}$ nmr $(CD_2CL_2)\delta p=71$ ppm.

To a solution of 2 [500 mg, 1.8 mmol] in $CH_2Cl_2$, $NEt_3$ [182 mg, 1.8 mmol] was added followed by $NMeH_2$ [0.450 ml of a 2M thf solution, 0.9 mmol]. The mixture was stirred for 30 mins and the solvent removed in vacuo. The solid was extracted with toluene and the resultant slurry filtered through celite affording a colourless solution. The solvent was again removed in vacuo to give $NMe\{P(C_6H_4OMe-2)_2\}_2$[420 mg, 1.6 mmol] as a white solid. Instead of extracting the solid using toluene it is possible instead to wash it using an alcohol, for example methanol, ethanol or isopropanol.

EXAMPLE 13

A carbon monoxide/ethene/propene terpolymer was prepared as follows: $CH_2Cl_2$ (80 cm$^3$) and propene (13.34 g 0.32 mol) were charged to a 300 cm$^3$ autoclave under nitrogen. The autoclave contents were then pressurised to 25 bar G with a 1:1 mixture of carbon monoxide and ethene and heated to 70° C. A solution of $B(C_6F_5)_3$ (0.169 g, 0.330 mmol) in $CH_2Cl_2$ (10 cm$^3$) was introduced followed by a further 10 cm$^3$ of $CH_2Cl_2$. Then the procatalyst solution comprising $(C_6H_4OMe-2)_2PN(Me)P(C_6H_4OMe-2)_2$ (0.008, 0.015 mmol), prepared as in Example 12, and palladium acetate (0.0035 g, 0.015 mmol) in $CH_2Cl_2$ (10 cm$^3$) was added, followed by an additional 10 cm$^3$ of $CH_2Cl_2$. The pressure was adjusted to 50 bar G by the addition of 1:1 carbon monoxide/ethene and this pressure was maintained by the addition of the aforementioned gas mixture on demand. After 1.5 hours the gas uptake had visibly slowed and after 3 hours no further gas uptake was observed. The polymer was collected by filtration and dried under reduced pressure. 15.30 gms of polymer was obtained containing 5.3 mole % of propene.

What is claimed is:

1. A compound of the formula

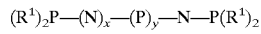

where x and y are independently 1 or 0 and $R^1$ is independently an aryl, alkyl, allcoxy, amido or substituted derivative thereof and at least one of the $R^1$ groups is an o-anisyl.

2. A compound as claimed in claim 1, having the formula

where $R^2$ is a hydrogen, a hydrocarbyl or hetero group.

3. A compound as claimed in claim 2 having the formula

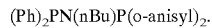

4. A compound as claimed in claim 2 wherein all $R^1$ groups are o-anisyl.

5. A compound as claimed in claim 4 wherein $R^2$ is methyl.

6. A process for preparing a compound as claimed in claim 4 comprising reacting $(o\text{-anisyl})_2PX$ where X is Cl, Br or F with $NH_2R^2$ where $R^2$ is as defined in claim 2 in the presence of a base.

7. A compound of formula II

  II where each L is independently a monodentate ligand or $L_2$ taken together is a bidentate ligand, P—P is a bidentate phosphine ligand having at least two phosphorus atoms joined by a bridging group of the formula —(N)$_x$—(P)$_y$—(N)— where x and y are independently 1 or 0, provided that when x=0 and y=0 L is not Cl and when L is Cl and P—P is $(R^7)_2PN(Me)N(Me)P(R^7)_2$, $R^7$ is not alkoxy.

8. A compound of formula III

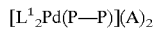  III where P—P is as defined in claim 7, $L^1$ is a neutral monodentate ligand or $L^1_2$ taken together is a neutral bidentate ligand and A is a weakly or non-coordinating anion or $(A)_2$ together is a weakly or non-coordinating dianion.

* * * * *